United States Patent

Kienzle

[11] 4,376,121
[45] Mar. 8, 1983

[54] ANTIALLERIGICALLY-ACTIVE IMIDAZOTHIENOPYRIMIDINE DERIVATIVES

[75] Inventor: Frank Kienzle, Flü, Switzerland

[73] Assignee: Hoffmann-La Roche Inc., Nutley, N.J.

[21] Appl. No.: 275,271

[22] Filed: Jun. 19, 1981

[30] Foreign Application Priority Data

Jun. 27, 1980 [CH] Switzerland ............ 4995/80

[51] Int. Cl.³ ............ A61K 31/505; C07D 595/14
[52] U.S. Cl. ............ 424/251; 544/250; 544/278; 549/68
[58] Field of Search ............ 544/250; 424/251

[56] References Cited

U.S. PATENT DOCUMENTS

| | | | |
|---|---|---|---|
| 3,932,407 | 1/1976 | Beverung, Jr. et al. | 544/250 |
| 4,159,377 | 6/1979 | Temple, Jr. | 544/278 |
| 4,230,707 | 10/1980 | Tinney et al. | 424/251 |
| 4,284,773 | 8/1981 | Ishikawa et al. | 544/247 |

FOREIGN PATENT DOCUMENTS 8408  3/1980  European Pat. Off. ............ 424/251

OTHER PUBLICATIONS

Sauter, et al., Monatshefte für Chemie, 109, (1), pp. 53-61 (1978).
Blaskiewicz, et al., Chemical Abstracts, vol. 83, 206324f (1975).

*Primary Examiner*—Donald G. Daus
*Assistant Examiner*—Diana G. Rivers
*Attorney, Agent, or Firm*—Jon S. Saxe; Bernard S. Leon; William G. Isgro

[57] ABSTRACT

Antiallergically-active pyrimidine derivatives of the formula wherein $R^1$ is hydrogen, chlorine, bromine or $C_{1-4}$-alkyl, and $R^2$ is hydrogen or methyl, prepared starting from corresponding 4-oxothieno-[3,2-d]pyrimidine derivatives, are described.

5 Claims, No Drawings

ANTIALLERIGICALLY-ACTIVE IMIDAZOTHIENOPYRIMIDINE DERIVATIVES

BRIEF SUMMARY OF THE INVENTION

The invention relates to antiallergically-active pyrimidine derivatives of the formula

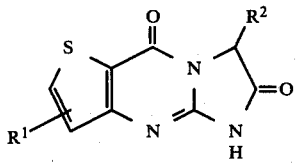

wherein $R^1$ is hydrogen, chlorine, bromine or $C_{1-4}$-alkyl, and $R^2$ is hydrogen or methyl.

The compounds of formula I are prepared from the corresponding 4-oxothieno-[3,2-d]pyrimidine derivatives.

In another aspect, the invention relates to compounds of the formula

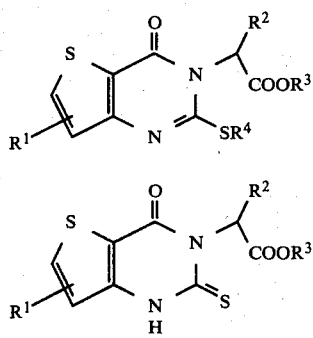

wherein $R^1$ is hydrogen, chlorine, bromine or $C_{1-4}$-alkyl and $R^2$ is hydrogen or methyl and $R^3$ and $R^4$ are $C_{1-4}$-alkyl, with ammonia.

DETAILED DESCRIPTION OF THE INVENTION

The invention relates to pyrimidine derivatives of the formula

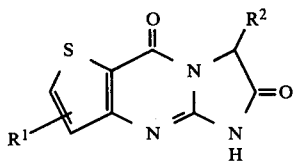

wherein $R^1$ is hydrogen, chlorine, bromine or $C_{1-4}$-alkyl and $R^2$ is hydrogen or methyl.

As used herein, the expression $C_{1-4}$-alkyl denotes straight-chain and branched groups, such as, methyl, ethyl, propyl and t-butyl.

Examples of compounds of formula I are:
Imidazo[1,2-a]thieno[3,2-d]pyrimidine-6,9(5H,7H)-dione;
7-methyl-imidazo[1,2-a]thieno[3,2-d]pyrimidine-6,9-(5H,7H)-dione; and
2- or 3-(methyl or chloro)-imidazo[1,2-a]thieno[3,2-d]-pyrimidine-6,9(5H,7H)-dione. The first-named compound is preferred.

The invention also relates to a process for the preparation of the compounds of formula I as well as pharmaceutical preparations based on the compounds of formula I.

The compounds of formula I can be prepared in accordance with the invention by reacting an ester of the formula

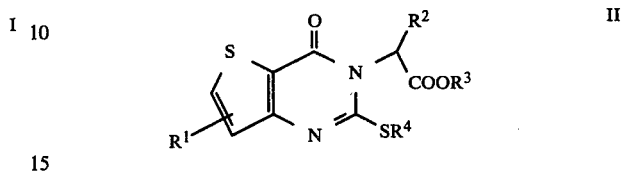

wherein $R^1$ and $R^2$ are as previously described and $R^3$ and $R^4$ are $C_{1-4}$-alkyl, with ammonia.

The ester of formula II can be reacted with a solution of ammonia in water or in an alcohol, for example, an alkanol such as methanol, at a temperature in the range of 0° to 150° C., preferably at about 120° C., conveniently under pressure. The reaction can also be carried out using liquid ammonia.

The compounds of formula I can exist in various tautomeric forms. Therefore, the invention is not limited to compounds of formula I depicted above, but also includes the tautomers, for example, compounds of the formulas

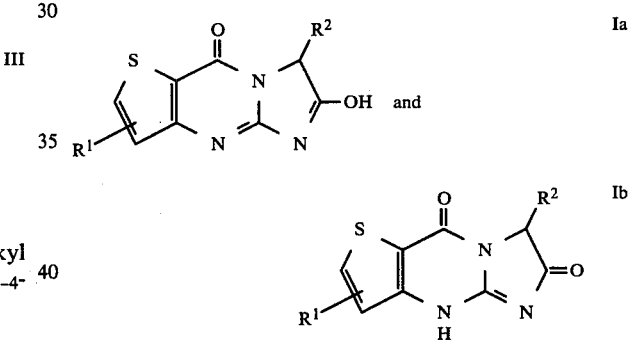

wherein $R^1$ and $R^2$ are as previously described.

The compounds of formula I wherein $R^2$ is methyl and their tautomers can, moreover, exist in the form of racemates or in optically active form, i.e., as the enantiomers, all of these forms are also part of the invention.

The esters of formula II can be prepared by reacting a compound of the formula

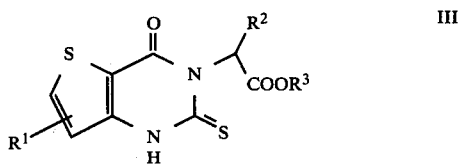

with a dialkyl sulfate of the formula $(R^4O)_2SO_2$ or a halide of the formula $R^4Hal$, wherein $R^1$, $R^2$, $R^3$ and $R^4$ are as previously described and Hal is halogen, preferably iodine. The reaction is conveniently carried out in the presence of a base, for example, an alkali metal carbonate such as potassium carbonate, in an aprotic solvent such as dimethylformamide, dimethyl sulfoxide or, when a dialkyl sulfate is used, also acetone, at a temperature in the range of 0° C. up to the reflux temperature of the reaction mixture, preferably while heating.

The compounds of formula III can be prepared by reacting a compound of the formula

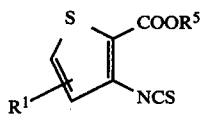

with an ester of the formula $$H_2N-\overset{R^2}{\underset{|}{CH}}-COOR^3,$$

wherein $R^1$, $R^2$ and $R^3$ are as previously described and $R^5$ is $C_{1-4}$-alkyl. The reaction is conveniently carried out in the presence of a base, for example, a trialkylamine such as triethylamine, in an aprotic solvent such as tetrahydrofuran, benzene or pyridine, at a temperature up to about 100° C., preferably at room temperature.

The compounds of formula IV can be prepared by reacting a compound of the formula

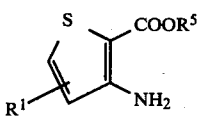

wherein $R^1$ and $R^5$ are as previously described, with thiophosgene, conveniently in the presence of a base, for example, an alkali metal carbonate, such as, sodium carbonate, or a trialkylamine, such as, triethylamine, in an apolar solvent such as, chloroform or carbon tetrachloride, at a temperature in the range of from between about −20° and 0° C.

In the compounds of formulas II, III, IV and V, $R^3$, $R^4$ and $R^5$ are preferably methyl.

The compounds of formulas II and III also form part of the invention.

The compounds of formula I are medicaments, particularly for the prevention of allergic reactions, for example, for the prophylactic treatment of bronchial asthma. The anti-allergic activity is demonstrated by the following experiment.

Male rats were sensitized by an intravenous injection of plasma containing antiovalbumin antibody (1 ml per animal). An anaphylactic bronchial asthma reaction was induced in the sensitized rats 18 hours later by an i.v. injection of ovalbumin (5 mg per kg). The breathing frequency and the ratio between expiration time and inspiration time were measured with the aid of a pneumograph as the measurement for this reaction. The test substances were administered orally, in the case of imidazo[1,2-a]thieno[3,2-d]pyrimidine-6,9(5H,7H)-dione ½ hour before the injection of the ovalbumin. The ability of the test substance to reduce the breathing frequency and the ratio of expiration time to inspiration time was taken as the measurement for the activity. An $ED_{50}$ of 32 mg/kg was thus found for the above named pyrimidine derivative. The test results are set out in the Table which follows.

| Dosage mg per kg | Breathing frequency | Decrease | Ratio expiration time/ inspiration time | Decrease |
| --- | --- | --- | --- | --- |
| 12.5 | 97.4 ± 13.7 | 32.1 | 403.9 ± 94.9 | 37.6 |
| 25 | 88.5 ± 20.7 | 38.0 | 357.5 ± 86.1 | 40.1 |
| 50 | 71.3 ± 53.9 | 53.9 | 210.7 ± 68.1 | 64.7 |

The compounds of formula I can be administered enterally, especially orally, or parenterally as antiallergic agents; for example, for the prophylactic treatment of bronchial asthma, with dosages fitted to individual requirements. The compounds of formula I can be administered therapeutically, for example, enterally, especially orally, or parenterally, by incorporating a therapeutic dosage in a usual dosage form such as tablets, capsules, elixirs, suspensions or solutions. The compounds of formula I can be administered in admixture with usual pharmaceutical carriers or binders such as maize starch, potassium stearate, magnesium carbonate, potassium silicate, dicalcium phosphate, talc or lactose. Moreover, they can be administered in the presence of buffers or agents used for adjusting the isotony. The pharmaceutical dosage forms can, when desired, be subjected to the usual pharmaceutical operations such as sterilization and the like. The pharmaceutical dosage forms can also contain other therapeutically valuable substances.

The amount of active substance, that is, a compound of formula I which is present in any of the dosage forms described above is variable. Capsules or tablets can contain, for example, about 10 mg to about 20 mg of a compound of formula I.

The frequency with which such a dosage form is administered to a patient, i.e., warm-blooded animal, varies and is dependent on the amount of active substance present in the dosage form and the needs and requirements of the patient. Under normal conditions, however, up to about 20 mg/kg of a compound of formula I can be administered daily in several dosages. It will, however, be understood that the dosages indicated above are only given by way of example and that they in no way limit the scope of the use of this invention.

The Examples which follow further illustrate the invention. All temperatures are given in degrees Centigrade, unless otherwise stated.

EXAMPLE 1

Preparation of imidazo[1,2-a]thieno[3,2-d]pyrimidine-6,9-(5H,7H)-dione

A mixture of 15 g of 2-methylthio-4-oxothieno-[3,2-d]pyrimidine-3(4H)-acetic acid methyl ester and 300 ml of methanol saturated with ammonia at −10° is stirred for 90 hours at 120° and 28 atmospheres. After cooling, insoluble constituents are removed by filtration and the filtrate is made acid with hydrochloric acid. The product is then removed by filtration and recrystallized from glacial acetic acid. Yield: 7 g of imidazo[1,2-a]thieno[3,2-d]pyrimidine-6,9-(5H,7H)-dione, melting point >250°; IR (in KBr): 3094 (s), 2746 (s), 1785 (s), 1764 (s), 1700 (s), 1644 (s), 1517 (s), 1440 (s), 1315 (m), 1219 (s), 1145 (m), 1049 (m), 790 (m), 732 (m).

The starting material can be prepared as follows:

To a mixture of 320 ml of chloroform, 120 ml of water and 55.4 g of sodium carbonate, stirred at 0°, are added dropwise 20 ml of thiophosgene, followed in the course of 15 minutes by 38.7 g of 3-amino-2-thiophenecarboxylic acid methyl ester hydrochloride. Then, the mixture is stirred at room temperature for 90 minutes. The organic phase is separated, dried and evaporated. The residue is recrystallized from chloroform-pentane. Yield: 42.5 g of 3-isothiocyanato-2-thiophenecarboxylic acid methyl ester, melting point 60°–61°.

A mixture of 38 g of glycine methyl ester, 380 ml of tetrahydrofuran and 40 ml of triethylamine is treated at room temperature with a solution of 42.5 g of 3-isothocyanato-2-thiophenecarboxylic acid methyl ester and stirred at room temperature for 20 hours. Then, the mixture is poured into water and the precipitated product is removed by filtration. Yield: 46.5 g of 1,4-dihydro-4-oxo-2-thioxothieno[3,2-d]-pyrimidine-3(2H)-acetic acid methyl ester, melting point 240° (decomposition).

A mixture of 46.5 g of 1,4-dihydro-4-oxo-2-thioxothieno[3,2-d]pyrimidine-3(2H)-acetic acid methyl ester, 875 ml of acetone and 110 g of potassium carbonate is treated with 45 ml of dimethyl sulfate and boiled under reflux for 3 hours. Then, the mixture is poured into water and the product is removed by filtration. Yield after recrystallization from ethyl acetate: 36 g of 2-methylthio-4-oxothieno-[3,2-d]pyrimidine-3(4H)-acetic acid methyl ester, melting point 167°–169°.

EXAMPLE 2

Preparation of 3-methylimidazo[1,2-a]thieno[3,2-d]pyrimidine-6,9-(5H,7)-dione

In an analogous manner to Example 1, starting from 30 g of 2-methylthio-7-methyl-4-oxothieno[3,2-d]pyrimidine-3-(4H)-acetic acid methyl ester there are prepared 15 g of 3-methylimidazo[1,2-a]thieno[3,2-d]pyrimidine-6,9-(5H,7H)-dione, melting point 12° (decomposition).

The starting material can be prepared in an analogous manner to Example 1 starting from 3-amino-4-methyl-2-thiophenecarboxylic acid methyl ester hydrochloride via 4-methyl-3-isothiocyanato-2-thiophenecarboxylic acid methyl ester (70 g, melting point 227°–228°) and 1,4-dihydro-7-methyl-4-oxo-2-thioxothieno[3,2-d]pyrimidine-3(2H)-acetic acid methyl ester (69 g, melting point 227°–228°); yield 68.9 g, melting point 131°–132°.

EXAMPLE 3

| Capsule formulation | mg/capsule | |
|---|---|---|
| | 10 mg | 20 mg |
| Imidazo[1,2-a]thieno[3,2-d]pyrimidine-6,9(5H,7H)-dione | 10.0 | 20 |
| Lactose | 215.0 | 205.0 |
| Maize starch | 60.0 | 60.0 |
| Magnesium stearate | 3.0 | 3.0 |
| Talc | 12.0 | 12.0 |
| Total | 300 mg | 300 mg |

The active substance imidazo[1,2-a]thieno[3,2-d]pyrimidine-6,9(5H,7H)-dione, lactose and maize starch are mixed in a suitable mixer. The mixture is ground through a suitable mill, mixed with the magnesium stearate and talc and filled on a capsule machine.

EXAMPLE 4

| Tablet formulation: | mg/tablet | |
|---|---|---|
| | 10 mg | 20 mg |
| Imidazo[1,2-a]thieno[3,2-d]pyrimidine-6,9(5H,7H)-dione | 10.0 | 20.0 |
| Lactose | 182.0 | 172.0 |
| Microcrystalline cellulose | 60.0 | 60.0 |
| Modified starch | 15.0 | 15.0 |
| Maize starch | 30.0 | 30.0 |
| Magnesium stearate | 3.0 | 3.0 |
| Total | 300 mg | 300 mg |

The active substance imidazo[1,2-a]thieno[3,2-d]pyrimidine-6,9(5H,7H)-dione, lactose, microcrystalline cellulose, modified starch and maize starch are mixed in a suitable mixer for 1 to 15 minutes. Then, the magnesium stearate is added and mixed for 5 minutes. The mixture is pressed on a suitable press.

EXAMPLE 5

| Wet granulation tablet formulation: | mg/tablet | |
|---|---|---|
| | 10 mg | 20 mg |
| Imidazo[1,2-a]thieno[3,2-d]pyrimidine-6,9(5H,7H)-dione | 10.0 | 20.0 |
| Lactose | 264.0 | 254.0 |
| Pregelatinized starch | 17.5 | 17.5 |
| Maize starch | 35.0 | 35.0 |
| Modified starch | 17.5 | 17.5 |
| Magnesium stearate | 6.0 | 6.0 |
| Total | 350 mg | 350 mg |

The active substance imidazo[1,2-a]thieno[3,2d-]pyrimidine-6,9(5H,7H)-dione, lactose and pregelatinized starch are mixed in a suitable mixer. The mixture is ground through a suitable mill, mixed with the modified starch and magnesium stearate and filled on a capsule machine.

I claim:

1. A compound of the formula

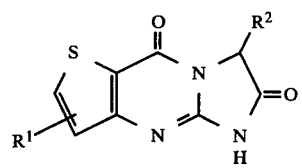

wherein $R^1$ is hydrogen, chlorine, bromine or $C_{1-4}$-alkyl and $R^2$ is hydrogen or methyl, or its tautomers, or, when $R^2$ is methyl, its racemates or enantiomers.

2. A compound in accordance with claim 1, imidazo[1,2-a]thieno[3,2-d]pyrimidine-6,9(5H,7H)-dione.

3. A compound in accordance with claim 1, 3-methylimidazo[1,2-a]thieno[3,2-d]pyrimidine-6,9-(5H,7H)-dione.

4. A pharmaceutical composition containing an antiallergically effective amount of a compound of the formula

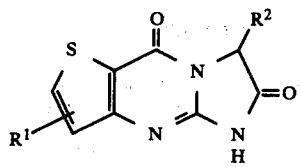

wherein $R^1$ is hydrogen, chlorine, bromine or $C_{1-4}$-alkyl and $R^2$ is hydrogen or methyl, or its tautomers, or when $R^2$ is methyl, its racemates or enantiomers, and a pharmaceutical carrier material.

5. A method for treating or preventing allergic reactions, which comprises administering an antiallergically effective amount of a compound of the formula

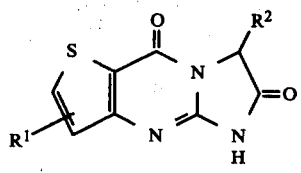

wherein $R^1$ is hydrogen, chlorine, bromine or $C_{1-4}$-alkyl and $R^2$ is hydrogen or methyl, or a tautomer thereof, or, when $R^2$ is methyl, a racemate or enantiomer thereof.

* * * * *